US00PP31640P2

(12) United States Plant Patent
Hansen

(10) Patent No.: US PP31,640 P2
(45) Date of Patent: Apr. 7, 2020

(54) ***HEUCHERA* PLANT NAMED 'GRAPE TIMELESS'**

(50) Latin Name: ***Heuchera* hybrid**
Varietal Denomination: Grape Timeless

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,864

(22) Filed: Jan. 24, 2019

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
CPC ... A01H 5/02; A01H 5/12; A01H 5/00; A01H 5/025; A01H 6/80; A01H 6/00
See application file for complete search history.

(56) References Cited

U.S. PATENT DOCUMENTS

PP20,935 P2 * 4/2010 Egger ..... A01H 5/02 Plt./440

OTHER PUBLICATIONS

Germania Seed Walters Gardens Bare Root and Plug Perennials 2019, retrieved on Sep. 24, 2019, retrieved from the Internet at https://www.germaniaseed.com/pdf/2019/749_walters.pdf, pp. 1,13,24. (Year: 2019).*

Park Seed Walter's Gardens 2019, retrieved on Sep. 24, 2019, retrieved from the Internet at https://parkseed.com/images/ART/WALTERS%202019.pdf, 2 pages total. (Year: 2019).*

* cited by examiner

*Primary Examiner* — June Hwu

(57) ABSTRACT

The new and distinct hybrid of *Heuchera* plant named 'Grape Timeless' with medium-sized, shallowly lobed, glossy foliage with rounded apices and lobes. Tightly-branched, upright panicles are produced from early summer to early fall for about fourteen weeks displaying large, bright, rosy-pink flowers. The new plant has a compact habit, is vigorous and produces showy, long-flowering, herbaceous, perennial mounds of leaves beginning the season purplish-red and developing a greyed-purple overlay and dark charcoal-purple surrounding the veins, effective as a specimen plant, en masse, or as a container plant in the landscape.

1 Drawing Sheet

Botanical denomination: *Heuchera* hybrid.
Variety denomination: 'Grape Timeless'.

STATEMENT REGARDING PRIOR DISCLOSURES UNDER 37 CFR 1.77(B)(6)

The first public disclosure of the claimed plant, in the form of a website to the public and email release to customers, was made by Walters Gardens, Inc. on Feb. 1, 2018 followed by the Walters Gardens, Inc. Summer 2018—Spring 2019 catalog. The first public sales of *Heuchera* 'Grape Timeless' was by Walters Gardens, Inc. on Jul. 23, 2018. Walters Gardens, Inc. obtained the new plant and information about the new plant directly from the inventor. No plants of *Heuchera* 'Grape Timeless' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of Coral Bells in the Saxifragaceae family and given the cultivar name of *Heuchera* 'Grape Timeless'. 'Grape Timeless' was hybridized by the inventor on Feb. 11, 2015 at a wholesale perennial nursery in Zeeland, Mich., USA. The seed or female parent was 'Berry Timeless' U.S. Plant Pat. No. 26,357 and the pollen or male parent was a proprietary unreleased hybrid known as 13-715-1.

*Heuchera* 'Grape Timeless' was first selected in the fall of 2016 and passed final evaluation in the fall of 2017 from among many other seedlings from the same cross and hundreds of other crosses and assigned the breeder code 15-42-2 through the remaining evaluation process. *Heuchera* 'Grape Timeless' has been asexually propagated initially by basal cuttings at the same nursery in Zeeland, Mich. in 2016 and also by sterile, shoot-tip, tissue culture propagation, and the resultant plants have remained stable and continued to exhibit the same characteristics as the original plant for multiple generations.

BRIEF SUMMARY OF THE INVENTION

The nearest comparison varieties include: the female parent 'Berry Timeless', 'Grape Expectations' U.S. Plant Pat. No. 26,894, 'Wildberry' U.S. Plant patent application Ser. No. 16/350,491, 'Wild Rose' U.S. Plant Pat. No. 29,923, and 'Electric Plum' U.S. Plant Pat. No. 29,924 and the two copending U.S. Plant Patent Applications 'Timeless Glow' U.S. Plant patent application Ser. No. 16/350,865 and 'Timeless Treasure' U.S. Plant patent application Ser. No. 16/350,856. 'Berry Timeless' has a similar profusion of flowers throughout the season but the flower color is lighter pink and the foliage is light green with slight silvering between the veins. 'Grape Expectations' has foliage with less dissected lobes and the flowers are larger, creamy-white for a shorter season and on taller stems. 'Wildberry' has less silver between the veins and the flowers are white and for a shorter period. 'Wild Rose' has more silver overlay on the leaf, the leaves and habit are larger and the flowers are present over a shorter season. 'Electric Plum' has lighter pink emerging leaves in the spring, the leaves are more rounded and light pink flowers are produced for a shorter season. The male parent has different colored foliage and the flowers are produced over a shorter period. 'Timeless Glow' has chartreuse-yellow foliage with a silver overlay and intense, rose-pink flowers for a similarly long period. 'Timeless Treasure' has small pewter leaves with dark mahogany veins and stems and large rosy-pink flowers for a similarly long period. *Heuchera* 'Grape Timeless' differs from its parents as well as all other coral bells known to the applicant in the following combined traits:

1. The medium-sized, flat, glossy foliage has rounded apices and lobes.
2. Leaf blades begin season purplish-red and develop greyed-purple overlay between the charcoal-purple area surrounding the veins.
3. Leaf blades are shallowly dissected with apices rounded and mucronulate.
4. Flowers are outwardly-facing, bright, rosy-pink on dark purple stems.
5. Flowering period begins in early summer and continues for about fourteen weeks into early fall with repeat panicles.
6. Compact, short-branched panicles of deep burgundy display flowers at multiple nodes beginning under foliage.
7. The new plant is vigorous and produces compact clumps and many individual leaves.

BRIEF DESCRIPTION OF THE DRAWINGS

The photographs of *Heuchera* 'Grape Timeless' demonstrate the overall appearance of the plant including the unique traits of a plant in a full sun trial block in Zeeland, Mich. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
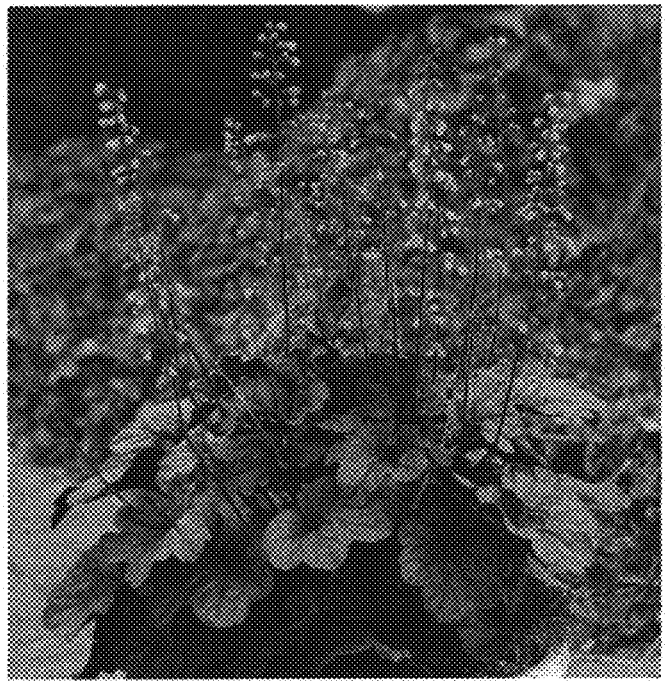
FIG. 1 shows a two-year-old plant grown in a container in a partially shaded greenhouse in peak flowering season.
Figure 2:
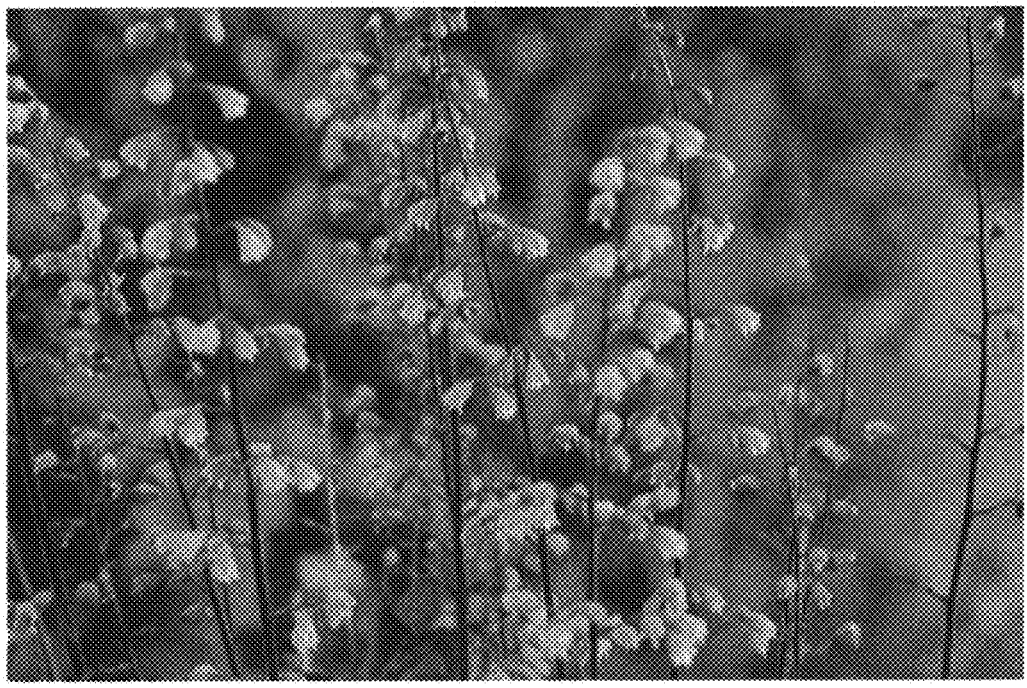
FIG. 2 shows a close-up of a flower panicle with buds and flowers from a two-year-old plant.

The following description is based on three-year-old plants growing in a partially shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was 'Berry Timeless', the male or pollen parent was the proprietary unreleased hybrid known only by the breeder code 13-715-1 consisting of 'Plum Royale' U.S. Plant Pat. No. 20,935, 'Georgia Plum' U.S. Plant Pat. No. 24,507, 'Mocha' U.S. Plant Pat. No. 18,386, 'Mocha Mint' (not patented), 'Pinot Noir' U.S. Plant Pat. No. 20,434 and 'Milan' U.S. Plant Pat. No. 21,682;

Plant habit: Hardy herbaceous perennial with basal rosette of foliage; mounded foliage about 27.0 cm tall and 40.0 cm in diameter with scapes to about 70.0 cm long; with about 6 stems per plant to about 3.0 cm long and 1.2 cm diameter at base, with about 20 to 35 leaves per stem; about 30 scapes during peak flowering;

Roots: Fibrous, finely branched;

Growth rate: Rapid, rooting from cutting in two weeks and finishing in three-liter container in about two and a half months;

Foliage: Cordate to nearly rounded; micro-puberulent adaxial and abaxial; palmately shallowly lobed with five main lobes shallowly dissected, less than one-quarter of the distance to the petiole; with few, typically four, shallow indentations; apex and lobe apices rounded and mucronulate; base cordate with basal lobes nearly overlapping to overlapping about 0.5 cm; margins crenate to mucronulate, ciliolate; lustrous adaxial and abaxial; held nearly horizontal; margin mostly flat;

Leaf blade size: To about 13.5 cm wide and 13.5 cm long, average about 11.5 cm wide and 11.5 cm long;

Leaf color: Spring and young emerging adaxial nearest RHS N186D around distal margin and nearest blend between RHS N186C and RHS N187B, thin region surround veins nearest RHS N187A; spring young emerging abaxial nearest RHS N186C; mature mid-season adaxial nearest RHS N187B with developing wider portion surrounding the veins nearest RHS N187A; abaxial mature mid-season nearest RHS 187A; fall and winter adaxial nearest N187B with undertone of nearest RHS 182B with portion surrounding veins nearest N187A; abaxial fall and winter RHS 187A;

Leaf quantity: Dense, about 140 per plant;

Veins: Palmate; sparsely hirsutulous and costate abaxial, glabrous and slightly impressed adaxial;

Vein color: Emerging or early spring adaxial and abaxial nearest RHS N186D; mid flowering season adaxial nearest RHS N186C, mid flowering season abaxial between RHS N186D and RHS N186C; late season adaxial variable, nearest RHS 197B and nearest RHS 187B proximally and distally becoming nearest RHS N187A, fall abaxial nearest RHS 187A;

Petiole: Cylindrical, base amplexicaul; pubescent with hairs to about 2.0 mm long; to about 21.0 cm long and 4.0 mm wide above stipule; average about 15.0 cm long and about 3.0 mm diameter above stipule;

Petiole color: Emerging leaf nearest RHS 187B; flowering season mature leaf nearest RHS 187A; late season nearest blend between RHS 177B and RHS 187B;

Stipule: Flared at base of petiole; glaucous abaxial and adaxial; margin ciliolate; to about 3.0 cm long and about 16.0 mm wide at base; with two lateral projections of about 5.0 mm long and 2.0 mm across in distal portion;

Stipule color: Young expanding adaxial and abaxial nearest RHS N186D; mature adaxial and abaxial nearest 187B with undertones nearest RHS 176B;

Peduncle: Panicle; terete; stiff; pubescent; upright; densely branched; to about 70.0 cm long and 4.5 mm diameter at base, average about 58.0 cm tall and 4.0 mm diameter; about 30 per plant with up to about 120 flowers per panicle, average about 100; initial flowers under foliage; tightly-branched panicle with up to 30 branches up to 5.5 cm long and 1.0 mm diameter decreasing distally, average 25 branches per panicle; lower branches mostly upright becoming outwardly distally; each branch subtended by foliar bract; flower density moderate;

Peduncle color: Nearest RHS 187A;

Foliar bract: Oblong palmate; incised margins to deeply lobed; apex acute; truncate clasping base; to 1.8 cm long and 1.0 cm across, decreasing distally; sessile;

Foliar bract color: Adaxial and abaxial nearest RHS 187A distally and nearest RHS N186D proximally;

Flowering longevity: Panicle effective for about two to four weeks; individual flowers about 5 days; self-cleaning;

Flowering period: Beginning early summer and repeating with new panicles without the need to remove old panicles through early fall for about 14 weeks;

Peduncle color: Nearest RHS 187A;

Pedicel: Cylindrical; puberulent; to about 7.0 mm long and 0.5 mm diameter, average about 5.0 mm long and 0.5 mm diameter; attitude outwardly;

Pedicel color: Nearest RHS 187A;

Buds one day prior to opening: Ellipsoid; rounded apex and attenuate base; puberulent to glandular; about 7.0 mm long and 3.5 mm diameter;

Bud color one day prior to opening: Nearest RHS 59C;

Flower: Perfect; campanulate; actinomorphic; about 9.0 mm long to tip of exserted style and 10.0 mm in diameter at corolla face;

Flower attitude: Outwardly;

Calyx: Base fused in proximal 3.5 mm to form hypanthium; puberulent to glandular abaxial, glabrous adaxial; about 8.0 mm long and 7.0 mm wide at apex;

Sepals: Five; lanceolate; acute apex, fused in basal 3.5 mm; to about 7.0 mm long and 3.0 mm wide at fusion;

Sepal color: Abaxial nearest RHS 59C, adaxial nearest RHS 59C with undertone of nearest RHS 146D toward apex;

Petals: Five; oblanceolate to spatulate; subacute apex and attenuate base; margin entire; glabrous adaxial and abaxial; about 4.0 mm long and 1.0 mm wide in middle;

Petal color: Abaxial and adaxial between RHS 70C and 70D;

Androecium: Five adnate to adaxial sepal about 1.0 mm above base;

*Filaments*.—Five, thin, glabrous; about 3.0 mm long and about 0.5 mm diameter; color nearest RHS NN155B.

*Anthers*.—Ellipsoidal, distinct, basifixed, longitudinal; about 1.0 mm long and about 0.7 mm across; color nearest RHS 167A.

*Pollen*.—Abundant; color nearest RHS 18B.

Gynoecium: One, two-beaked; half-inferior; bifid style with pistil split at ovary; about 9.0 mm long;

*Style*.—Bifid; split apart at apex of ovary; exserted; about 5.0 mm long and about 0.5 mm diameter; color nearest RHS 60C.

*Stigma*.—Acute apex, about 0.1 mm diameter; color nearest RHS 75A.

*Ovary*.—Half-inferior, about 4.0 mm long and 3.0 mm diameter; ellipsoidal to globose; acute apex and base rounded; color lighter than RHS 146D.

Fruit: Small two-beaked capsule; about 2.5 mm long and 2.5 mm across; drying to RHS 200C;

Seeds: Abundant; slightly flattened ellipsoid; about 0.3 mm long, 0.2 mm across and about 0.1 mm thick; color nearest RHS 200A;

Disease and pest tolerance: The new plant grows best with ample moisture and drainage in either part sun or full shade. Cold hardy from USDA zones 4 to 9. Other resistance and tolerance outside of that normal for *Heuchera* is not known.

It is claimed:

1. The new and distinct Coral Bells plant named *Heuchera* 'Grape Timeless' as herein described and illustrated.

* * * * *